United States Patent [19]

Boone

[11] Patent Number: 4,961,343
[45] Date of Patent: Oct. 9, 1990

[54] METHOD FOR DETERMINING PERMEABILITY IN HYDROCARBON WELLS

[75] Inventor: Daniel E. Boone, Houston, Tex.

[73] Assignee: IDL, Inc., Houston, Tex.

[21] Appl. No.: 382,900

[22] Filed: Jul. 19, 1989

Related U.S. Application Data

[63] Continuation of Ser. No. 266,258, Oct. 31, 1988, abandoned, which is a continuation of Ser. No. 37,037, Apr. 10, 1987, abandoned, which is a continuation-in-part of Ser. No. 818,024, Jan. 19, 1986, Pat. No. 4,765,182.

[51] Int. Cl.$^5$ .............................................. E21B 49/00
[52] U.S. Cl. ........................................ 73/152; 73/38; 73/155; 175/50
[58] Field of Search ................... 73/38, 149, 151, 152, 73/153, 154; 166/250; 175/48, 50

[56] References Cited

U.S. PATENT DOCUMENTS

| | | | |
|---|---|---|---|
| 2,214,674 | 6/1940 | Hayward | 73/153 |
| 2,328,555 | 9/1943 | Hoover, Jr. | 73/155 |
| 2,342,273 | 2/1944 | Hayward | 73/51 |
| 2,346,203 | 4/1944 | Zaikowsky | 73/51 |
| 2,694,923 | 4/1954 | Carpenter | 73/153 |
| 2,714,308 | 8/1955 | Heck | 73/153 |
| 2,749,748 | 6/1956 | Slobod et al. | 73/153 |
| 2,883,856 | 4/1959 | Youngman | 73/23 |
| 2,938,117 | 9/1960 | Schmidt | 250/255 |
| 3,031,571 | 4/1962 | Fearon | 250/52 |
| 3,386,286 | 2/1968 | Moore | 73/153 |
| 3,462,761 | 8/1969 | Horeth et al. | 346/1 |
| 3,495,438 | 2/1970 | Mangum | 73/19 |
| 3,512,164 | 5/1970 | Bynum | 346/1 |
| 4,286,461 | 9/1981 | Bres et al. | 73/155 |
| 4,298,572 | 11/1981 | Moffet et al. | 422/68 |
| 4,319,482 | 3/1982 | Bunner | 73/153 |
| 4,342,222 | 8/1982 | Alekhin et al. | 73/153 |
| 4,347,736 | 9/1982 | Mamadzhanov et al. | 73/155 |
| 4,536,713 | 8/1985 | Davis et al. | 324/324 |
| 4,546,640 | 10/1985 | Stone et al. | 73/19 |
| 4,555,934 | 12/1985 | Freeman et al. | 73/38 |
| 4,608,859 | 9/1986 | Rockley | 73/153 |
| 4,635,735 | 7/1987 | Crownover | 73/155 |

FOREIGN PATENT DOCUMENTS

| | | | |
|---|---|---|---|
| 1388016 | 3/1975 | United Kingdom | 73/38 |
| 2027910 | 2/1980 | United Kingdom | 73/38 |

Primary Examiner—Hezron E. Williams
Assistant Examiner—Kevin D. O'Shea
Attorney, Agent, or Firm—Darryl M. Springs

[57] ABSTRACT

During oil and gas well drilling operations, at the wellsite surface the percentage by volume of hydrocarbon gas present in the return drilling fluid is monitored in order to determine the percentage of gas saturation in the formation. Rate of penetration of the drill bit is monitored as well. A pore saturation function is derived wherein anomalously low values thereof relative to expected values for productive zones indicate flushing ahead of the drill bit of hydrocarbons out of the pore volume of cuttings in the return fluid. A mud filtrate flow rate is then determined from the drilling rate, gas saturation, and formation porosity. Pressure differential in the vicinity of the drill bit is also determined, comprised of the difference between the drilling fluid column pressure and pore pressure. Formation permeability is then directly determined in real time during the drilling operation from a functional relationship between the filtrate flow rate, pressure differential, and viscosity of the drilling fluid.

8 Claims, 4 Drawing Sheets

METHOD FOR DETERMINING PERMEABILITY IN HYDROCARBON WELLS

This is a continuation of application Ser. No. 266,258 filed Oct. 31, 1988, which was a continuation of application Ser. No. 037,037, filed Apr. 10, 1987, which was a continuation in-part of application Ser. No. 818,024, filed Jan. 13, 1986, now issued as U.S. Pat. No. 4,765,182.

FIELD OF THE INVENTION

This invention relates to systems and methods for deriving measurements relating to subsurface earth formations during oil and gas well drilling operations and, more particularly, relates to such systems and methods for determining formation permeabilities in real time.

BACKGROUND OF THE INVENTION

In the search for hydrocarbon bearing subsurface earth formations, various systems and methods have been devised for determining parameters which provide indications of such formations and their potential commercial value. One such parameter which is extremely important in assessing the commercial producibility of an oil field is permeability, known in the literature as "k" measured in darcies. The reason for the importance of this parameter is that it is intended to provide a quantitative indication of the expected rate of hydrocarbon flow through the formation and borehole. This in turn is quite important from a commercial standpoint in determining the commercial feasibility of producing a well inasmuch as the formation permeability will be directly related to the potential rate of hydrocarbon production from the well.

Due to the importance of such a parameter, various techniques and apparatus have been devised which sought to arrive at reliable determinations for permeability. Basically, these techniques involved two approaches, namely the analysis of physical core samples of the formation or the interpretation of data derived from logging instruments lowered into the borehole.

With respect to core samples, the desired permeability measurement was made from laboratory testing of the sample. However, in the case of well logging data, permeability was conventionally obtained by an empirical functional relationship between permeability and porosity, the latter of which was sought to be measured by various well logging or "wire-line" techniques.

These aforementioned techniques for seeking to measure the highly valuable permeability parameter were fraught with numerous difficulties. In the case of core sampling, the physical method of obtaining a sample of a subsurface earth formation and retrieving it at the surface for physical analysis immediately suggests many obvious such difficulties. First, there is the expense of such a system in providing for a reliable retrieval mechanism. Secondly, the samples obtained were frequently too small or inaccurate to provide reliable statistical information. For example, it will be appreciated that in the coring process, the formation is damaged and may be contaminated by flushing and invasion of the drilling fluid which may then comprise a portion of the sample retrieved.

Furthermore, by the time the sample is retrieved at the surface and transported to the laboratory for analysis, the sample has undergone many changes which indicate that an inference is not always reliable that parameters measured from the sample are indicative of the actual formation characteristics. For example, hydrocarbons once present in the sample when in place in the formation may have long since left the sample, rendering subsequent tests on the sample unreliable. Still further, only a limited number of discrete samples could be obtained practically, and thus it was often frequently difficult to decide what borehole increment to core.

In the case of well logging data, such techniques likewise suffer from serious deficiencies in attempts to arrive at a reliable determination of permeability. First, it must be appreciated that the effects of hydrocarbons in situ on the various parameters being measured by wireline techniques will be less than those detected by the techniques of the present invention wherein hydrocarbons are detected in their expanded state at the surface. Secondly, wireline techniques exhibit similar difficulties to cure samples in terms of problems presented by a borehole of varying diameter, and drilling fluids therein.

For example, in the various wireline techniques for measuring porosity from which permeability is determined (which may include neutron, acoustic, or induction logging), the technique is to generally measure a parameter from a wireline tool disposed within the borehole wherein the correct parameter sought to be measured is a property out in the formation. Accordingly, this measurement must be made through the borehole wall, drilling fluid, and filtercake. Frequently the wireline data is thus not only measuring the desired formation parameter but also measuring the effects of the borehole and materials therein. In other words, the filtercake, drilling fluids, and the like are adversely affecting the desired formation parameter being measured.

Various techniques have been attempted to alleviate this problem such as borehole compensation wherein a deep measurement into the formation and a shallow one indicative of materials within the borehole are made, the latter being used to compensate for the effects of measuring through these materials in the deep measurement. Nevertheless, difficulties associated with this problem continue to plague the industry. For example, formation density measurements from which porosity and in turn permeability may be determined are typically adversely affected quite obviously by higher drilling mud weights. Moreover, these well logs are also seriously affected by unknown variations in other parameters such as the resistivity of formation water or drilling mud which must be known for accurate formation measurements.

From the foregoing, it is thus not surprising to find that prior determinations of permeability have suffered from numerous deficiencies. First, such permeability values are determined inferentially from questionable data and indirectly from empirical functional relationships between permeability and porosity. Such values for permeability have in many cases been known to be erroneously low, and, accordingly, various "fudge factors" have been known to be introduced in recognition of the unreliability of previous determinations of such permeability.

Even more important, however, is the serious drawback relating to when the questionable permeability measurements are even made available. Because it is necessary to retrieve a core sample for analysis or to cease the drilling operation to permit lowering of the wireline instrumentation package, these important indications of permeability have heretofore not been readily available in real time during the actual drilling operation. Thus, not only would it be highly desirable to have an improved and more accurate technique for making direct determinations of formation permeability, but to be able to do so continuously and in real time during the drilling operation.

These and other deficiencies of the prior art have been overcome by the systems and methods of the present invention, which will be described hereinafter in greater detail with reference to the accompanying drawings.

SUMMARY OF THE INVENTION

A system and method for determining permeability of a subsurface earth formation in real time during an oil and gas well drilling operation is disclosed.

The volume of drilling fluid circulated in an ongoing drilling operation is measured at the wellsite surface per a preselected vertical increment of formation drilled. The volume of total hydrocarbon gas in the drilling fluid volume is also periodically monitored at the surface, from which a percentage hydrocarbon gas by volume in the drilling fluid may be determined. From the known drillbit diameter and the drilling rate, the volume of formation drilled per the preselected vertical borehole increment and circulated drilling fluid volume is determined. The percentage gas in drilling fluid parameter is then correlated to this volume of formation drilled to yield a percentage gas per unit of volume of formation drilled or percentage gas saturation as a function of borehole depth. These values are corrected from wellsite surface conditions to borehole pressure and temperature conditions at the borehole elevations corresponding to the depth at which the formation volumes were drilled. A function GASAT is accordingly derived corresponding to gas saturation per unit of formation drilled corrected to borehole pressure and temperature conditions at successive borehole elevations.

During the drilling operation, values are also measured as a function of drilling depth for the rate of penetration of the drill bit (ROP), viscosity of the drilling fluid ($\mu$), formation porosity ($\phi$), pore saturation (PORESAT, from GASAT/$\phi$), hydrostatic drilling fluid pressure or mud weight (MW), and pore pressure (PP). In a preferred embodiment, porosity is determined from ROP functionally related to time (T), according to the formula $\phi = 100 - (\log_{10}T \times 28.12)$, where T=drilling time in seconds and is functionally related to ROP as the time to drill each foot of pentration of the drillbit, and the term "28.12" is a dimensional constant ($C_1$). In order to obtain a correct value for porosity under known conditions, interpretation sets a shale baseline nominally to 7% or a matrix rock to 4% in carbonate rocks.

For each porosity value at a given borehole depth an expected preselected regionally known value for gas or pore saturation is derived and compared to the actual surface measured GASAT or PORESAT. If the expected value exceeds the actual GASAT value by a preselected magnitude, flushing by the drilling fluid of hydrocarbons into the formation is indicated and must be accounted for in the permeability determination in accordance with the present invention.

A percentage of a unit volume of drilled formation flushed by drilling fluid (PF) is then determined from the relationship $PF = (S_1 - PORESAT)/S_1$, where $S_1$ = the regionally expected value for pore saturation (nominally 70% in the Gulf Coast area and within a range of 60-80%).

Linear drilling fluid penetration or fluid flow rate (FFR) through this unit volume is then given by $FFR = PF \times ROP$, and is converted to a volumetric flow rate Q by the equation: $Q = FFR \times \phi \times C$, where C = a dimensional constant conversion factor depending on the units being used.

Pressure differential ($\Delta P$) across this unit volume is then determined from $\Delta P = (MW-PP) \times D \times C$, where L = depth or length of unit volume in the formation and C = a dimensional constant conversion factor which may, in one unit system, be 0.052, converting lbs./gal. to psi/ft. of depth. Permeability k is then determined from the reservoir flow relationship:

$$k \text{ millidarcies} = (Q \times \mu \times L = 1000)/(\Delta P \times A)$$

where
L = the length of the unit volume (which in the aforesaid unit system may be 1 cm.),
$\mu$ = the viscosity of fluid flowing through the porous sample, and
A = the cross sectional area of flow through the unit volume (which in the aforesaid unit system may be 1 cm.).

It will be noted that k is normally expressed relative to Darcy units, wherein a Darcy is the flow through a sample, having an area A of 1 $cm^2$ and a length of 1 cm, of water having a viscosity $\mu$ of 1 centipoise, with a pressure differential across the sample being 1 atmosphere (14.6969 psi).

Permeability k is thereby determined analogously to determination of permeability by testing of a formation core sample, wherein, by analogy, the aforementioned $\Delta P$ is the pressure differential across the core sample during testing, Q is the volumetric flow rate of a test fluid through the core sample, and $\mu$ is the viscosity of the test fluid.

DETAILED DESCRIPTION OF THE INVENTION

Figures 1, 2:
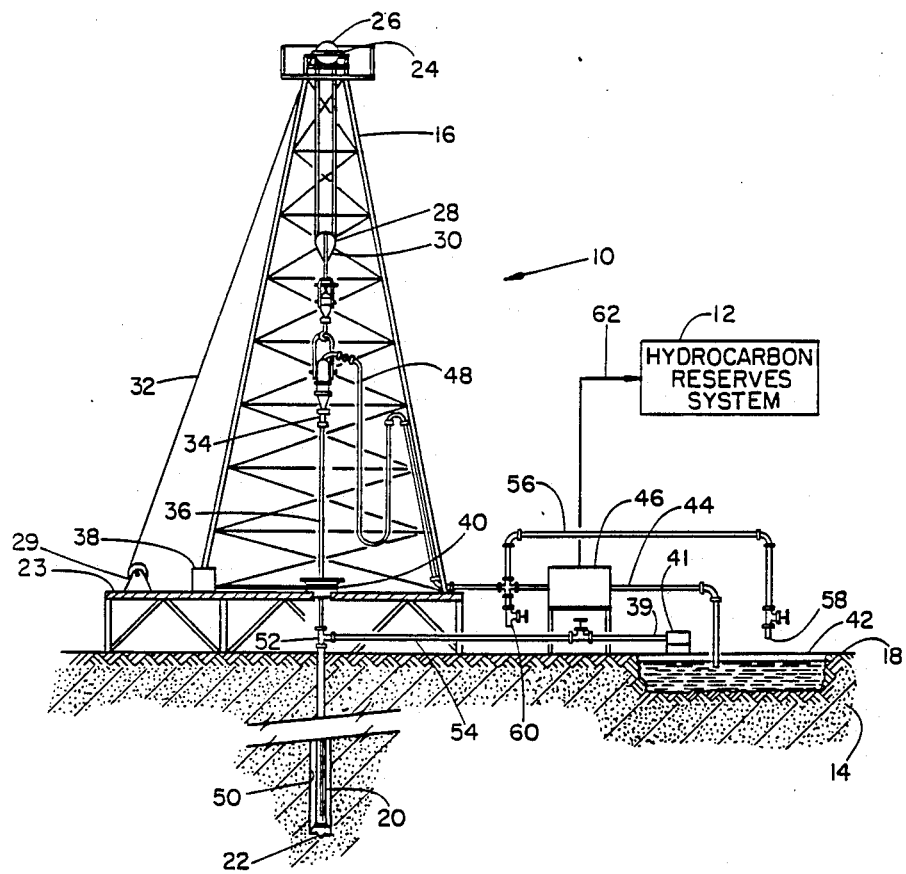
FIG. 1 is an illustration, partly schematic and partly in section, depicting a typical surface oil and gas well drilling equipment system to which the invention is applicable.
FIG. 2 is a schematic diagram indicating in greater detail the components comprising the hydrocarbon reserves system depicted in FIG. 1.

With reference to FIG. 1, a rotary drilling system 10 will be seen generally depicted therein for drilling oil and gas wells in subsurface earth formations 14. A derrick 16 is provided which rests upon the earth surface 18 for purposes of supporting, raising, lowering, and rotating a drill pipe string 20 during drilling operations as well as for delivery and rotation of other tubular goods and devices in the borehole.

Disposed at the distal end of drill string pipe 20 is a rotary drill bit 22 for penetrating the formation 14 upon rotation thereof as hereinafter described. At the uppermost portion of derrick 16, a crown block 24 may be seen carrying a pulley 26. A motor 38 resting on platform 23 has extending therefrom a drilling cable 32 which traverses a pulley 29. From the pulley 29, the cable 32 extends over the pulley 26 and thence is repeatedly routed between pulley 26 and a pulley 28 carried by traveling block 30 which is pendantly disposed from the cable 32.

A swivel 34 hangs from the block 30 having attached thereto a kelly 36 for purposes of imparting a rotary motion to the drill string 20 in a manner well known in the art. In operation, the purpose of the cable 32, motor 38, pulleys 26, 28, and 29, and blocks 24 and 30 are primarily to provide for vertical upwards and downwards movement of the drill string 20 so as to permit connection and disconnection of drill pipe sections to the string 20 as desired.

Still referring to FIG. 1, a rotary table 40 is provided in platform 23 for imparting rotary motion to the drill string 20 during the drilling operation. A sump 42 adjacent the platform contains drilling fluid entering and exiting from the borehole. An inlet pipe 44 is further included for withdrawing drilling fluid from the sump 42 and delivering it to a suitable mud pump 46. A hose 48 in turn, receives the mud pumped from the pump 46 and delivers it through the swivel 34, kelly 36, rotary table 40, and bell nipple 52 into the annulus defined by the drill pipe 20.

In the conventional manner, mud from the sump 42 thus delivered into the interstices of the drill pipe 20 will circulate downwards therethrough and about the bit 22 thereby lubricating it and carrying away cuttings from the formation 14. The circulating drilling fluid will thence, as a result of the pumping operation, travel upwards between the outer wall surface of the drill pipe 20 and the borehole wall 50 until it reaches the aforementioned drill collar. At the nipple 52, it will be noted that a discharge pipe 54 will be provided for receiving this upwardly moving drilling fluid which contains the cuttings made by the bit 22. The drilling mud will thence be discharged out the end of outlet pipe 39 through a screen 41 and back into the sump 42. A bleeder line 56 may further be provided which may selectively route mud from the sump 42 through the pump 46 and back to the sump 42, discharging at the end 58 of the bleeder line 56. Additionally, a mud faucet 60 may be provided interconnected to the hose 48, again, for selectively withdrawing mud from the pump 46 as desired. It will be appreciated that the hereinbefore described general drilling system has been greatly simplified inasmuch as numerous components and variations well known in the art have been omitted. For example, it is conventional in the art to provide for delivery of return mud from the discharge pipe 54 into a "possum belly" tank (not shown), the overflow thereof being delivered into a shale shaker for purposes of reducing the cuttings content of the return mud prior to its return to the sump 42. In like manner, it is further conventional to provide for degaser equipment whereby when the mud becomes excessively gas cut thereby reducing its effective weight and ability to provide a sufficient hydrostatic head for prevention of blowouts and the like, the degaser will draw a vacuum on the return mud so as to draw the undesirable gas carried therein out of the mud. Accordingly, it will be appreciated that the invention is not intended to be limited to any one particular drilling operation system and admits of numerous variations thereof as being within the scope of the present invention.

Still referring to FIG. 1, there will further be seen depicted therein a schematic block diagram captioned hydrocarbon reserve system 12 which will be hereinafter described in greater detail. The system 12 is shown as being functionally interconnected to the rotary drilling system 10 by means of data line 62. Whereas, in the figure, this line 62 is shown as originating from the pump 46, it is merely intended to schematically indicate that various parameters and measurements to be hereinafter described may be derived from the various components of the drilling system 10 and electronically delivered on the line 62 to the system 12 for purposes to be hereinafter described. For example, as will be discussed in greater detail hereinafter, date relating to the volume of mud being pumped by the pumper 46 as well as chemical and volumetric analysis of the gas contained within the mud in the sump 42 will be desired. This line 62 is thus intended to indicate delivery of the necessary data to the system 12 for derivation of such parameters and mathematical and electronic operation thereon as hereinafter described.

Now that the overall system has been described, a general description of the theory and principles of the present invention will be given. This will be followed by a detailed description of the hydrocarbon reservoir system 12 of FIG. 1 depicted in greater detail and FIG. 2, whereby the purposes of the system and components thereof will thus be made more clear. In accordance with the present invention, during drilling operations, it is first desirable to derive periodically a measurement of the volume of drilling fluid being circulated through the drill string 20 per vertical linear foot of formation drilled. This may be done by means of an electrical signal from the pump 46. More particularly, by knowing the number of strokes of the pump per linear foot drilled, and the pump capacity in terms of mud volume pumped per stroke, the desired mud volume per linear drilled foot may be obtained.

Next, it is desirable to derive measurement of the percentage of hydrocarbon gas by volume present at the surface and at atmospheric pressure conditions at surface temperatures in each such measured volume of drilling fluid per linear foot drilled and being returned to the sump 42. Various techniques well known in the art for accomplishing this are available, such as the familiar "hot-wire" method. In this technique, mud from the discharge pipe 54 is routed through a mud trough or possum belly (not shown) primarily to catch drill cuttings. A gas extractor in the mud trough at the end of the mud flow line 54 agitates mud with a stirring device to release gas entrained in the mud. The gas is routed to a hot-wire gas detector which detects gas volume per volume of mud. An appropriate computer or signal processor may then interrogate the gas detector periodically (such as at 5 second intervals) to derive a periodic average measurement of volumetric percentage of gas in the mud, as for example, such an average being derived per linear foot drilled.

With the volume of drilling fluid circulated per linear foot drilled being known and the percentage gas (by volume) entrained in the mud (averaged over periodic time intervals), it is further necessary to determine the volume of formation drilled through for the given vertical foot of formation. This volume per linear foot drilled is assumed to be a constant cylindrical volume and, accordingly, varies as the square of the diameter of the bit.

It may also be periodically made available in an appropriate signal processor and at appropriate preselected depth intervals. For example, formation volume drilled for each vertical foot may be derived by any convenient means employing a periodic depth interrupt signal and depth data produced by a depth system or other mechanism at preselected increments of borehole depth.

It is assumed that the gas which evolved and was measured from the volume of mud which circulated per linear foot drilled came from the rock volume of formation drilled through, inasmuch as the cuttings from the formation volume will be suspended in the volume of mud. Accordingly, it will be appreciated that by multiplying the percentage gas in the mud volume per foot drilled by the mud volume circulated per linear foot drilled, the result will be the gas volume entrained in the mud. Moreover, by dividing this gas volume in the mud by the volume of formation drilled per linear foot, the gas saturation of percentage of gas in the volume of formation per foot drilled will be given.

It will be appreciated that the aforementioned percentage gas saturation is at surface conditions of pressure and temperature, inasmuch as the hydrocarbon gas is detected at the surface. However, hydrocarbon reserves are typically defined at borehole conditions. Thus, it may be desirable to convert this gas saturation percentage to an equivalent corresponding to the borehole depth at which the cuttings become entrained in the mud volume under consideration. This may be accomplished by borehole pressure and temperature gradient conversion factors well known in the art, resulting in percentage of hydrocarbon volume at borehole pressures and temperature conditions attributable to the rock volume.

The apparatus of the present invention will further desirably be provided with means for periodically detecting the ratio of light to heavy hydrocarbons, thus providing an output proportional to $C_1/C_2$, where $C_1$=methane gas and $C_2$=ethane gas. It is generally accepted in the art that such a ratio within a range of 2-6 corresponds to an oil and wherein a range of 6-50 corresponds to a gas. Such apparatus may conveniently take the form of a gas chromatograph which samples gas from the preselected mud volume and analyses it quantitatively in a well known manner to derive measurements of $C_1$, $C_2$, $C_3$, and $C_4$ present in the mud.

Accordingly, for the volume of mud and formation under consideration, a multiplier conversion factor is selected as a function of the ratio determined for the mud and formation volume in question. More particularly, if the ratio is 2-6, a conversion factor of 7758.34 is selected corresponding to a Bbl/acre-foot familiar to the art. Conversely, if the ratio is found to be between 6–50, the conversion factor of 43.56 is selected corresponding to MCF/acre-foot at borehole temperatures.

It will thus be appreciated that by multiplying the previously described gas saturation values by the particular conversion factor in functional relation to the ratio just described, a volumetric indication in terms of volume of either oil or gas in Bbl/acre-feet or MCF/acre-feet is thereby provided for the preselected linear borehole foot.

Moreover, it will further be appreciated that the hereinabove described process may be repeated for successive one foot increments of borehole or at any other increments. This may be done by deriving, for successive such increments, corresponding measurements of formation volume per linear foot drilled, drilling fluid volume circulated per linear foot drilled, and gas volume per such drilling fluid volume. By combining these parameters in the manner just described, translating the result to borehole temperature and pressure conditions, and applying the appropriate conversion factor (dependent upon the $C_1/C_2$ ratio determined for the gas in the mud over the interval), the volume indication of hydrocarbon reserves in place at borehole pressure and temperature conditions in the next increment of borehole may be arrived at. Still further, by totallg such values corresponding to adjacent increments of borehole, total potential hydrocarbon reserves in place for a show or formation bed of any width desired may be readily determined at downhole conditions.

The mathematical functional relationships hereinabove described are as follows:

% GAS SATURATION =  Equation 1

$$\frac{(\% \text{ Gas})(Bbl \text{ Mud})(5.6146)(14.65)(460 + BHT)}{(14.65 + BHP)(460 + 100)} \times \frac{1}{(.00545 \ D^2)}$$

where
% GAS SATURATION or "% GASAT"—Volume of hydrocarbons in a cylindrical formation volume one foot high with a diameter "D" at BHT and BHP conditions, in percent D = Bit diameter in inches % Gas = Hydrocarbon gas volume per unit volume of circulated drilling fluid at surface conditions, in percent BHT = Bottomhole temperature in °F. at borehole elevation where formation volume originated (measured or calculated from borehole elevation)

BHP = Bottomhole pressure in psi at borehole elevation where formation volume originated (measured or calculated from borehole elevation)

Bbl = volume of drilling fluid circulated downhole per vertical borehole foot drilled.

Hydrocarbon reserves volume at Bottomhole Pressure and Temperature Conditions

FOR GAS $<6 < C_1/C_2 < 50>$   Equation 2

VOLUME (in MCF/Acre-Foot) =

$$\% \text{ GAS SATURATION} \times \frac{1}{100} \times 43.56$$

FOR OIL $(2 < C_1/C_2 < 6)$   Equation 3

VOLUME (in Bbl/Acre-Foot) =

-continued $$\% \text{ GAS SATURATION} \times \frac{1}{100} \times 7758.34$$

Where
43.56 and 7758.34 are conversion factors for converting a unit volume of formation to MCF/acre-foot or Bbl/acre-foot, respectively.

Now that a generalized theoretical discussion of the principles of the present invention has been given, the purposes of the components depicted in FIG. 2 may be more readily understood. Accordingly, with reference to FIG. 2, the hydrocarbon reserves system 12 of FIG. 1 will be seen depicted therein in greater detail. From the foregoing, it will be recalled that it is desirable to periodically obtain measurements of the drilling fluid volume per linear foot drilled. Accordingly, the module indicated by reference number 70 is intended functionally to perform this function as a component part of the system 12. As aforesaid, this may be done by means of any convenient electrical system. It will be recalled that in one such convenient system as previously described, the module 70 may receive on the signal line 62 from the drilling system 10 parameters such as depth interrupts indicating the successive passage of the drill bit 22 through preselected borehole increments. Also carried on line 62 may be constants preset in the module 70 indicating the incremental Bbl per stroke of the mud pump 46, as well as signals indicating the number of such strokes which have transpired between successive such depth interrupts. From such parameters, the mud volume detector 70 may generate an electrical signal output on line 72 indicating the volume of mud or drilling fluid circulated through the drill string 20 pre preselected increment of linear borehole depth drilled such as on a per foot basis, with such data being delivered on line 72 to an appropriate computer 74.

It will further be recalled that in accordance with the teachings of the present invention, it is desirable to derive for the aforementioned mud volume detected by the module 70 a volume of entrained gas within such mud volume. Accordingly, the line 62 being delivered to the gas detector 76 of the system 12 is further intended to schematically depict that, as previously described with respect to the mud trough, the gas detector may be any convenitent such detector well known in the art for deriving such a measurement. More particularly, in one embodiment, means will be provided in the mud trough for agitating the mud and collecting samples thereof which are volumetrically measured by the gas detector 76 for example on a time basis increment of 5 seconds or the like. An electrical signal indicated by line 78 is thence delivered by the gas detector 76 to the computer 74 (shown for convenience as being delivered through the chromatograph 60 and thence on line 82 to the computer 74). The gas detector 76 may also receive depth interrupts on line 62 in like manner to those delivered to the mud volume detector 70, such depth interrupts being generated by the computer 74 in response to depth pulses from the sheave wheel of the drilling system 10. Upon receipt of such depth interrupts, the gas detector 76 will deliver to the computer 74 the currentmost 5-second integrated gas volume. The computer 74 may thence relate this last value of the gas volume to the last value for mud volume per foot drilled delivered to the detector 70. The computer 74 may thence calculate a gas volume detected per mud volume measured for a given borehole increment such as one foot, so as to derive a percentage of gas entrained in the mud at the surface.

Also, with the foregoing theoretical discussion in mind, it will be noted from FIG. 2 that a chromatograph 80 is provided. In response to gas samples delivered on the line 78 from the gas detector 76, the chromatograph 80 will periodically continue to recalculate light to heavy hydro-carbon ratios $C_1/C_2$ in the aforementioned manner. Again, in response to appropriate depth interrupts from the computer 74, the chromatograph module 80 may deliver on line 82 digital signals to the computer 74 corresponding to the latest time average of such a ratio or the value for such a ratio corresponding to gas detected in a mud voluem circulated per foot drilled as indicated from the module 70.

Figure 3:
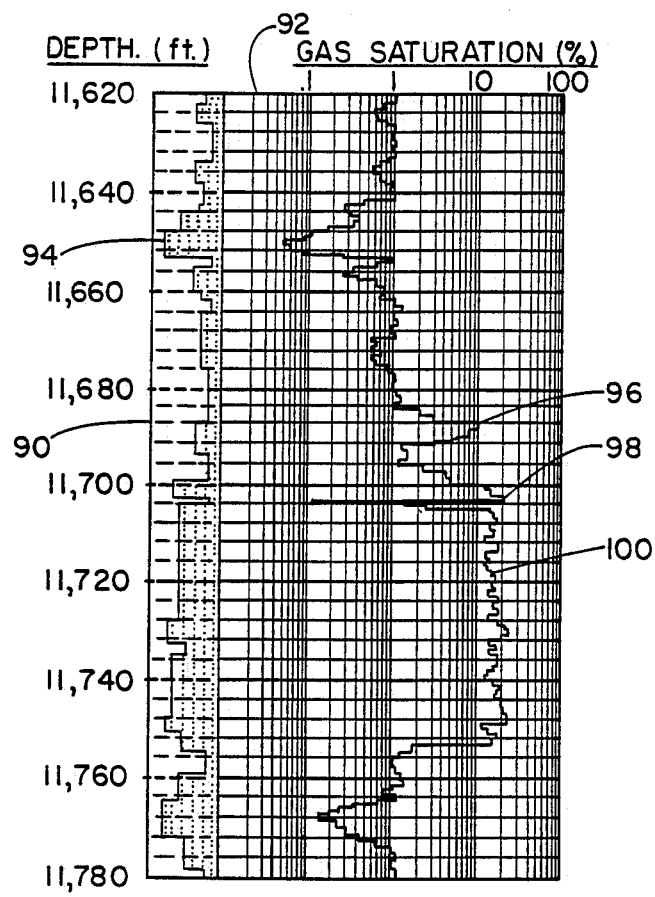
FIG. 3 is a representative well log obtained in accordance with the practice of the invention.

Additionally stored in the computer 74 will be the previously described conversion factors well known in the art for converting surface pressure and temperatures to borehole conditions as well as the conversion factors for converting gas saturations to MCF/acre-feet and the Bbl/acre-feet. Also contained in the computer 74 will be routines for calculating the $C_1/C_2$ ratios, and further subroutines for calculating the desired hydrocarbon reserves at each desired borehole increment in functional response to the hereinabove noted functional relationships. As aforesaid, depth interrupt information being delivered to the computer 74 will enable the computer to correlate the various measurements for mud volume per foot drilled, gas volume in the mud volume per foot drilled, gas volume in the mud volume per foot drilled, and chromatograph detection signals so as to ensure that proper values are functionally multiplied together corresponding to the appropriate parameter data derived at corresponding borehole depths. Finally, with reference to FIG. 2, it will be noted that the computer 74 is schematically depicted as having an output 84 delivered to an appropriate display device 86 and storage 88. It may be desirable for the hydrocarbon reserve volumetric data to be displayed in some convenient form, as for example, in the manner of a logarithmic strip chart well known in the art wherein such values are successively displayed corresponding to successive increments of borehole depth. Similarly, it may be desirable simply to store computer digital values carried by line 84 in appropriate digital storage 88 for subsequent processing. It will be appreciated that the format and content of information shown in display 86 and stored in the storage 88 may vary widely in accordance with the desired format and informational content and the like. Accordingly, the invention is not intended to be so limited to any particular display or sets of data stored. For example, in some applications it may be desirable to print out in real time a logging curve corresponding to actual hydrocarbon reserve volumes as a function of borehole depth. However, in other such applications, it may be sufficient merely to provide, as indicated in FIG. 3, a logging curve corresponding simply to the percentage of gas saturation, i.e., the percentage of hydrocarbon volumetrically per volume of formation. Upon subsequent analysis of the analysis and interpretation of the log, these gas saturation values at subsequent borehole depths may be manually multiplied by the appropriate conversion factor (either MCF/acre-feet or Bbl/acre-feet) corresponding to the $C_1/C_2$ ratios and other analytical factors in order to determine actual hydrocarbon reserve volumes.

With reference now to FIG. 3, there will be seen depicted therein, an illustration of the present invention showing logging data derived from an actual oil and gas well located in southern Louisiana. First, it will be noted from reference numeral 90 that the ordinate indicates borehole depth in feet and, for the segment of the log therein depicted, the borehole increment of interest ranges from 11,620 to 11,780 feet.

Still referring to FIG. 3, with respect to the abscissa 92, it will be recognized as a conventional logarithmic scale wherein the previously described gas saturation parameter in percent is indicated. Also included in the log of FIG. 3 is a lithology curve 94 derived from porosity data and the like wherein the dotted segments indicate relative proportion of sand. Superimposed on the logarithmic portion of the log of FIG. 3 will be seen the actual log trace 96 corresponding to the gas saturation values described herein. It will be noted from the log that three zones of interest have been identified by reference numerals 96, 98, and 100 referring, respectively, to interval A at depth 11,689–11,691, interval B at depth 11,698–11,702, and interval C corresponding to the depth interval 11,705–11,753.

With reference to the accompanying table, the aforementioned intervals A–C may be seen to have listed associated therewith percentage gas saturation values (at bottomhole conditions) calculated in accordance with the method described herein from values of mud volume per foot drilled, gas volume per mud volume (i.e., percentage gas in mud), the $C_1/C_2$ ratios and the like (not shown). In the column captioned "Reserves in Interval of Interest" numbers will be seen listed therein corresponding to surface reserves calculated for each appropriate depth interval in accordance with the hereinbefore noted functional relations defined in the equations previously described. A representative example of derivation of a calculated reserve listed in Table 1 for the borehole depth of 11,701 feet will follow hereinafter for clarity:

TABLE 1

| DEPTH | POROSITY | % GASAT | PORSAT | SW | SURFACE RESERVES VOLUME AT STANDARD PRESSURE (14.65 psi) & STANDARD TEMPERATURE (65° F.) | RESERVES IN INTERVAL OF INTEREST |
|---|---|---|---|---|---|---|
| 11687 | 10 | 3.0 | 30 | 70 | | |
| 88 | 10 | 3.0 | 30 | 70 | | |
| 89 | 17 | 10.2 | 60 | 40 | 1878 : | Interval A (96) |
| 90 | 16 | 8.8 | 55 | 45 | 1620 : 3' | 4566 MCF/ |
| 91 | 13 | 5.9 | 45 | 55 | 1068 : | Acre-Foot |
| 92 | 10 | 3.0 | 30 | 70 | | |
| 93 | 9 | 1.3 | 14 | 86 | | |
| 94 | 11 | 1.5 | 14 | 86 | | |
| 95 | 11 | 1.5 | 14 | 86 | 276 | |
| 96 | 9 | 1.3 | 14 | 86 | 239 | |
| 97 | 11 | 2.2 | 20 | 80 | 405 | |
| 98 | 14 | 4.5 | 32 | 68 | 828 : | |
| 99 | 15 | 4.5 | 32 | 68 | 828 : | Interval B (98) |
| 11700 | 20 | 14.0 | 70 | 30 | 2578 : 5' | 11506 MCF/ |
| 1 | 25 | 17.5 | 70 | 30 | 3222 : | Acre-Foot |
| 2 | 31 | 22.0 | 72 | 28 | 4050 : | |
| 3 | 3 | 0.4 | 14 | 86 | 74 | |
| 4 | 10 | 1.4 | 14 | 86 | 258 | |
| 5 | 13 | 2.6 | 20 | 80 | 479 : | |
| 6 | 20 | 13.0 | 65 | 34 | 2394 : | |
| 7 | 22 | 15.0 | 67 | 33 | 2762 : | |
| 8 | 25 | 17.5 | 70 | 30 | 3222 : | |
| 9 | 23 | 15.0 | 65 | 35 | 2762 : | |
| 10 | 24 | 16.0 | 67 | 33 | 2946 : | |
| 11 | 24 | 17.0 | 71 | 29 | 3130 : | |
| 12 | 21 | 14.0 | 67 | 33 | 2578 : | |
| 13 | 26 | 19.0 | 73 | 27 | 3498 : | Interval C (100 |
| 11714 | 26 | 18.0 | 69 | 31 | 3314 : | 145, 841 MCF/ |
| 15 | 22 | 14.0 | 64 | 36 | 2578 : | Acre-Foot |
| 16 | 22 | 15.0 | 68 | 32 | 2762 : | |
| 17 | 20 | 13.0 | 65 | 35 | 2394 : | |
| 18 | 21 | 14.0 | 67 | 33 | 2578 : | |
| 19 | 23 | 16.0 | 69 | 31 | 2946 : | |
| 20 | 24 | 17.0 | 71 | 29 | 3130 : | |
| 21 | 24 | 16.0 | 67 | 33 | 2956 : | |
| 22 | 23 | 15.0 | 65 | 35 | 2762 : | |
| 23 | 23 | 15.0 | 65 | 35 | 2762 : | |
| 24 | 22 | 15.0 | 68 | 32 | 2762 : | |
| 25 | 26 | 18.0 | 70 | 30 | 3314 : | |
| 26 | 26 | 17.0 | 65 | 35 | 3130 : | |
| 27 | 25 | 18.0 | 72 | 28 | 3314 : | |
| 28 | 20 | 13.0 | 64 | 36 | 2394 : | |
| 29 | 26 | 18.0 | 70 | 30 | 3314 : | |
| 30 | 29 | 21.0 | 72 | 28 | 3866 : | |
| 31 | 31 | 22.0 | 71 | 29 | 4051 : | |
| 32 | 29 | 20.0 | 69 | 31 | 3682 : | |
| 33 | 23 | 15.0 | 65 | 35 | 2762 : | |
| 34 | 27 | 17.0 | 63 | 37 | 3130 : | |
| 35 | 25 | 15.0 | 60 | 40 | 2762 : | |
| 36 | 27 | 17.0 | 63 | 37 | 3130 : | |

TABLE 1-continued

| DEPTH | POROSITY | % GASAT | PORSAT | SW | SURFACE RESERVES VOLUME AT STANDARD PRESSURE (14.65 psi) & STANDARD TEMPERATURE (65° F.) | RESERVES IN INTERVAL OF INTEREST |
|---|---|---|---|---|---|---|
| 37 | 28 | 19.0 | 68 | 32 | 3498 : | |
| 38 | 25 | 16.0 | 64 | 36 | 2946 : | Interval C (100 |
| 39 | 23 | 15.0 | 65 | 35 | 2762 : 49' | (continued) |
| 40 | 21 | 13.0 | 62 | 38 | 2394 : | 145, 841 MCF/ |
| 41 | 26 | 17.0 | 65 | 35 | 3130 : | Acre-Foot |
| 42 | 27 | 18.0 | 67 | 33 | 3314 : | |
| 43 | 26 | 18.0 | 69 | 31 | 3314 : | |
| 44 | 24 | 17.0 | 71 | 29 | 3130 : | |
| 45 | 26 | 18.0 | 69 | 31 | 3314 : | |
| 46 | 27 | 18.0 | 67 | 33 | 3314 : | |
| 47 | 29 | 20.0 | 69 | 31 | 3682 : | |
| 11748 | 32 | 22.0 | 69 | 31 | 4050 : | |
| 49 | 31 | 22.0 | 71 | 29 | 4050 : | |
| 50 | 19 | 11.0 | 58 | 42 | 2025 : | |
| 51 | 22 | 13.0 | 59 | 41 | 2393 : | |
| 52 | 23 | 14.0 | 61 | 39 | 2578 : | |
| 53 | 20 | 13.0 | 65 | 35 | 2393 : | |
| 54 | 12 | 1.8 | 15 | 85 | 331 | |
| 55 | 13 | 1.3 | 10 | 90 | 239 | |
| 56 | 13 | 1.3 | 10 | 90 | 239 | |
| 57 | 15 | 1 | 7 | 93 | 184 | |
| 58 | 23 | 1.1 | 5 | 95 | 202 | |
| 59 | 20 | 1.2 | 6 | 94 | 221 | |
| 60 | 20 | 1.4 | 7 | 93 | 258 | |

Example-

| | |
|---|---|
| Depth | 11,701 Feet |
| Bit Size | 8.75 inches |
| % Gas in Mud (measured at surface) | 20.5% |
| Mud Volume (circulated per linear foot of formation drilled at 11,701 feet) | 28.4 Barrels |
| Bottomhole Temperature (at 11,701 feet) | 271° F. |
| Bottomhole Pressure (at 11,701 feet) | 8578 psi |
| Surface Gas Sample Temperature | 100° F. |
| Atmosphere Pressure | 14.65 psi |

From Equation 1:

$$\% \text{ GAS SATURATION} = \frac{(\%Gas)(Bbl\ Mud)(5.6146)(14.65)(460 + BHT)}{(.00545\ D^2)(BHP + 14.65)(460 + 100)}$$

$$= \frac{(20.5\%)(28.4\ Bbl)(5.6146)(14.65)(460 + 271)}{(8.75)^2 (.00545)(8578 + 14.65)(460 + 100)} = 17.5\%$$

This value corresponds to the entry in the "%GASAT" column at 11,701 feet of Table 1.

It will be noted that in the intervals B and C, a $C_1/C_2$ ratio between 6–50 was detected indicating presence of gas and accordingly Equation 2 is employed.

It will further be noted that in Table 1 reserves are shown at *surface* conditions (i.e., standard temperature, pressure). Accordingly, the fact that the % GASAT measurements are at borehole conditions at 11,701 feet (Equation 2) means they must be compensated for when applied to yield surface reserves as follows:

| | |
|---|---|
| Standard Atmospheric Pressure (SP) = | 14.6 psi |
| Standard Atmospheric Temperature (ST) = | 65° F. |

$$\text{Surface Reserve Volume} = \text{Equation 2} \times \frac{(BHP + SP)(460 + ST)}{(SP)(460 + BHT)}$$

$$= (17.5\%) \times \frac{1}{100} \times \frac{43.56(8578 + 14.6)(460 + 65°)}{(14.6)(460 + 271°)}$$

$$= 3222\ \text{MCF/Acre-Foot}$$

Still with reference to Table 1, it will be noted in the far right column captioned "Reserves in Interval of Interest" that the calculated reserves per foot listed for all the depth intervals of the particular interval have been summed to yield a combined total of hydrocarbon reserves for the entire borehole increment comprising the interval. It is of significant interest to note that in accordance with the present invention, the intervals A–C were determined to be productive sands, such interpretation being borne out by sidewall cores. However, it is even further of note that conventional electric wireline logs condemned the sands in these intervals of interest as being water wet and accordingly non-productive.

Several additional aspects of the invention herein disclosed must be noted. First, it should be readily apparent that a time lag exists between location of the drill bit 22 at a praticular borehole depth and when drilling fluid adjacent the bit at that depth has finally traversed up the entirety of the borehole to the well site surface wherein such mud sample may be analyzed. In other words, in real time as a mud sample is being analyzed at the surface, the characteristics thereof in terms of gas volume entrained therein and the like will not correspond to borehole elevations at which the drill bit 22 is positioned during such analysis. Rather, such analysis of a given mud sample at the surface will correspond to a shallower borehole depth at which the bit 22 and uphole sample were positioned earlier in time. Accordingly, means must be provided which are well known in the art for "lagging" the data to compensate for this time lag between current indicated depth and the prior shallower depth at which surface mud samples were located when they are undergoing current analysis at the surface. The degree of such lag compensation is obviously functionally related to the drilling rate and may be accounted for in the data by the computer 74 and in manners well known in the art.

Also, it has been found that shale lithology has the most reliable gas saturation inasmuch as it is a compacted rock of uniform structure exhibiting very little difference in pore space from one form of shale to another. Accordingly it has been found empirically that the gas saturation of shale normally falls within the area of approximately 1% gas saturation, i.e., a "shale line" well known in the art should be set to indicate approximately a 1% gas volume presence in the rock. Thus, it is conventional practice to employ multipliers on the individual data points appearing on the log, such as those of FIG. 3, in order to ensure that these data points corresponding to the shale line in fact appear substantially about the 1% gas saturation coordinate. The reason for the necessity for such compensation is well known in the art and includes such factors as the gas traps for detecting gas having defective paddles, or being set too high in the mud trough so as to draw too much air giving too low a gas reading, or the like.

Still further, it will be recalled that when the $C_1/C_2$ ratio was found to be approximately within the ranges of 6–50 and 2–6, presence substantially of gas for oil was assumed respectively. Accordingly, corresponding Equations 2 or 3 were employed to apply the appropriate correction factor to the percentage GASAT parameter to convert to MCF/acre-feet (for gas) or Bbl/acre-feet (for oil).

However, it will be appreciated that choice of such ranges for $C_1/C_2$ ratios is to a certain extent subjective and arbitrary and the invention is accordingly not intended to be so limited. For example, reservoirs will typically be comprised of a combination of oil and gas reserves. Thus, it is contemplated by the present invention to apply appropriate conversion factors to the percentage GASAT parameter in functional relation to a characterization of the reservoir in terms of relative presence of gas and oil however determined. Moreover, it will be noted that the conversion factors employed are in terms of conventional units of hydrocarbon volume well known in the art such as MCF/acre-feet in the case of gas and Bbl/acre-feet in the case of oil, although the invention is not intended to be so limited. Accordingly, the percent GASAT parameter may be multiplied by any appropriate constant conversion factor dependent upon the characterization of the reserve in terms of relative oil and gas content to yield a volumetric reservoir hydrocarbon determination in terms of any desired unit which may, if desired for example, be metric equivalents thereof.

In the foregoing disclosure, measurement of gas saturation at the surface has been converted to downhole pressure and temperature conditions for reservoir determinations. However, it will be readily apparent that it is within the scope of the present invention to omit such conversion to these downhole conditions if desired.

More particularly, gas saturation is calculated to downhole condition for quantitative reference. However, the cubic feet of gas determined at the surface per one foot of formation would provide the measured gas reserve per foot at surface conditions as reserves are normally expressed.

Now that a clear understanding has been gained of the manner in which the invention makes a real time determination of gas saturation during the drilling operation by monitoring the gas detected in the return drilling fluid at the surface, another feature of the invention employing this determination will be hereinafter described in greater detail, namely the real time determination of formation permeability from surface-measured gas saturation values.

Figure 4:
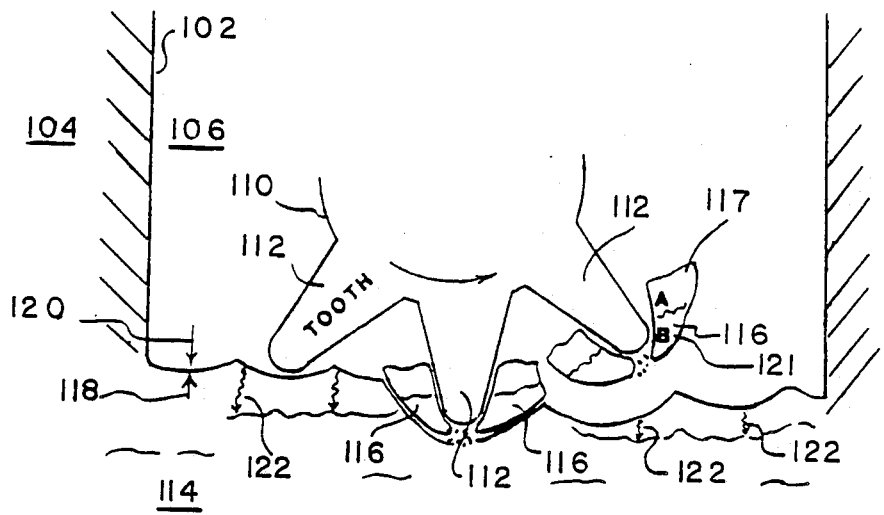
FIG. 4 is an elevational view showing schematically a drill bit acting on a formation and demonstrating relation thereof to parameters measured and used in accordance with the teachings of the present invention.
Figure 5:
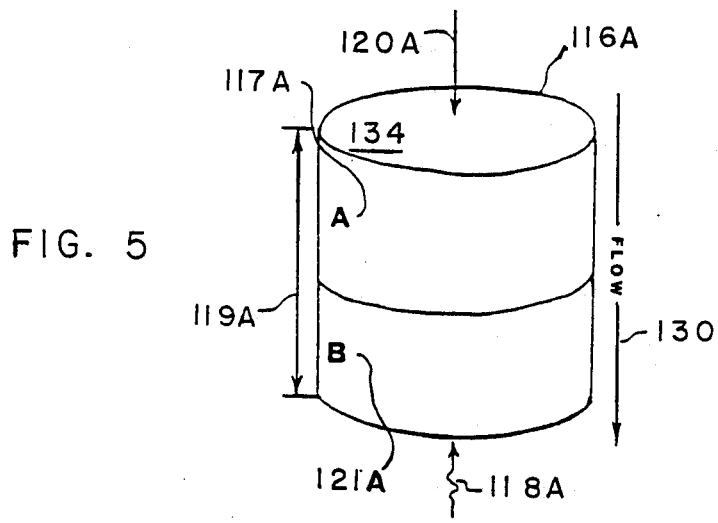
FIG. 5 is a pictorial and enlarged view of an increment of borehole depicted in FIG. 4 showing the flow of drilling fluid therethrough.

First, with reference to FIG. 5, a brief discussion will be provided of the conventional manner for determining a permeability "k" by testing of a core sample derived from the downhole formation. With reference to FIG. 4 this will then be followed by a more detailed look at the downhole environment adjacent the drill bit in order to draw physical analogies between the parameters employed in conventional core sample permeability analysis and the parameters relating to this drilling situation employed in the present invention for real time permeability analysis. Finally, with reference to FIG. 6, a typical example of a well log will be discussed showing actual permeability determination values made in accordance with the teachings of the present invention, with a comparison to similar values determined from conventional core sample analytical methods.

Detailed explanation of the determination of "k" by conventional core sample flow testing may be seen in an article in SPE Transactions, Dec. 1983, Volume 269, Section 2, by Nur et al, with particular reference to page 455.

With reference to FIG. 5 in more detail now, there will be seen depicted therein schematically a core sample 116A derived from any conventional core sampling technique wherein a portion of the formation is retrieved by a downhole tool and transmitted to the surface for analysis. To enhance understanding of the analogy between the techniques of the present invention and conventional core sample analysis, whenever possible reference numerals relative to the present invention depicted in FIG. 4 will find correlative counter-part reference numerals followed by an "A" in FIG. 5. Thus, for example, a drilling cutting or section separated from the formation by operation of the rock bit will carry a designation 116 in FIG. 4 and is correlative to an actual physical core sample cut from the formation and carrying a designation reference numeral 116A in FIG. 5.

Referring once again to FIG. 5, this core sample 116A, after being retrieved from the subsurface environment and transmitted to a testing laboratory will conventionally be subjected to a test wherein a fluid having a known viscosity is made to flow through the sample 116A (which has a predetermined geometry) under controlled conditions by establishment of a known pressure differential across the sample. From the flow rate of the fluid through the core sample, permeability may thence be determined in accordance with a functional relationship hereinafter set forth.

Thus, with reference to FIG. 5, this core sample 116A will be introduced into an appropriate testing facility wherein a hydrostatic pressure differential is introduced across the sample (shown schematically as the hydrostatic pressure difference between pressure exerted by fluid in the direction of arrow 120A less the pressure exerted by fluid on the other side of the sample in the direction of arrow 118A). The greater pressure on the upper portion of the sample 116A will cause a flow of the test fluid, having a known viscosity, through the sample in the direction of flow arrow 130. The sample 116A will, of course, prior to being subjected to the test described herein, be carefully measured to establish its nominal cross sectional area 134 and length 119A.

Inasmuch as the sample 116A is permeable to some degree, the test fluid will accordingly flow through the sample, thus filling up to some degree the interstitial pore space therein as the fluid flows through the sample. In accordance with a conventional relationship well known in the art for permeability "k", by measuring this flow rate through the sample, permeability thereof may be determined in accordance with the functional relationship wherein k is in milli-darcies of:

$$k = (Q \times \mu \times L \times 1000)/\Delta P \times A),$$

where
Q = the flow rate through the sample,
$\mu$ = viscosity of the fluid,
L = the sample length,
A = the sample cross section, and
$\Delta P$ = the pressure across the sample.

Once this permeability value has been determined for the core sample, it is then inferentially reasoned that this permeability value corresponds to the permeability of the formation at the elevation within the borehole at which the core sample was retrieved. For the foregoing numerous reasons hereinbefore set forth, such assumptions are not always accurate. For example, the core sample undergoes physical changes during its transfer from the high temperature and high pressure borehole environment to the lab, including the loss of hydrocarbons therein. Also it will be recalled that inasmuch as the physical mechanisms for obtaining the sample require penetration through the drilling fluid, such materials will typically be present in the sample and thus render its proper analysis more difficult and questionable. Moreover, the volume of the test sample is typically so small relative to the formation volume of interest that oftentimes even a core sample which has retained its integrity may not be representative of the vast formation volume of interest.

The present invention has contemplated that the logging operation is in effect continuously providing drilling cuttings analogous to core samples through which drilling fluid flows. By measuring during the drilling operation parameters analogous to those hereinbefore described with respect to core sample analysis for permeability determination, a real time determination of permeability during the drilling operation may be achieved.

For a given known formation porosity in a formation expected to be productive, a GASAT (determined in accordance with the teachings of the invention) determined at the surface may be made. If however this value, determined by detecting the relative amounts of gas in the return drilling fluid is less than a regionally expected value, it may be assumed that a portion of this expected gas has been flushed from the pore spaces of the cuttings by the drilling fluid. Schematically with reference to the core sample 116A, this percentage of the pore space of the sample 116A which has been flushed by the drilling fluid may be seen represented as portion A designated by reference numeral 117A of the sample, whereas the non-flushed portion is represented as B or numeral 121A.

This difference between the expected and known gas saturation values is functionally related to the amount of drilling fluid flushing. Moreover, flow rate of the drilling fluid into the formation and the cuttings is functionally related to the rate of penetration of the drill bit. Thus, it will be appreciated that this fluid flushing volume and flow rate may be seen to be analogous to the volume of fluid flowed through the core sample at the measured rate to determin permeability. Moreover, as will be seen with reference to FIG. 4 in greater detail, the pressure differential across the core sample 116A is analogous to a pressure differential established by the difference between the hydrostatic head pressure of the mud colum (MW) 120A and the pore pressure 118A (PP) of the formation.

Accordingly, it is specifically contemplated by the present invention that, by monitoring these aforementioned parameters which are analogous to the physical parameters employed in core sample analysis for permeability, these analogous parameters may be employed in the previously noted permeability equation for the desired real time permeability determination during a drilling operation.

The analogy between these parameters may be seen more clearly with reference to FIG. 4 which is intended to show schematically the operation and interrelationships between the drilling fluid, rock bit, and formation which is being cut away by the drilling operation. A formation 104 is traversed by a borehole 102 which conventionally has suspended therein a drill string having on the end a drill bit cutter 110. Surrounding the drill string and drill bit is a column of drilling fluid 106.

The drilling bit 110 includes a plurality of teeth 112 which operate in a rotary fashion against the bottomhole 114 portion of the formation 104 so as to break off drill cuttings 116. These cuttings are carried to the surface suspended in the drilling fluid 106. As previously described the column of drilling fluid 106 will establish a hydrostatic head pressure or downward mud weight (MW) shown by reference numeral 120. Counteracting this, of course, is the pressure exerted by the fluids within the interstitial spaces of the formation bottom 114, shown schematically by the pore pressure (PP) arrow 118. This pressure differential, given by $\Delta P$ may be seen to be analogous to the pressure differential across the core sample of FIG. 5.

With continued reference to FIG. 4, in comparison to FIG. 5, it will be noted that these various drill cuttings 116 may be seen to be analogous to the core sample 116A of FIG. 5. In like manner, these cuttings 116 may be thought of schematically as having a volumetric portion 117 wherein the pore volume is flushed by the drilling fluid and a remaining portion 121 which has not been flushed.

In FIG. 4 the operation of the drilling fluid in flushing hydrocarbons from the pore space into the formation and thus replacing them in the drilling cuttings (which explains the GASAT values being lower than anticipated) may be seen schematically represented by the arrows 122 indicating flushing into the bottom hole portion 114 of the formation 104. Finally, with respect to analogies between the drilling situation of FIG. 4 and the core analysis of FIG. 5, it will be readily appreciated that the viscosity of the test fluid flowing through the core sample 116A is analogous to viscosity of the drilling fluid 106 of FIG. 4 which flushes into a portion of the pore volume of the cuttings 116.

In accordance with the present invention, during a drilling operation, values are thus measured as a function of drilling time (T) for the rate of penetration of the bit (ROP), viscosity of the drilling fluid ($\mu$), porosity ($\phi$), pore saturation (PORESAT), gas saturation in accordance with the invention regarding derivation from gas content in the return drilling fluid (GASAT), hydrostatic fluid pressure (MW), and pore pressure (PP). It will be noted in passing that although such porosity values may be determined in a number of ways well known in the art, in a preferred embodiment such porosity has been found to be functionally related to time (T) derived from ROP in accordance with the previously given equation.

These values are used in accordance with the invention periodically to determine permeability as follows, with reference to typical numbers by way of example. With a predetermined porosity of, for example, 23%, gas in the volume A and B (i.e. the sample 116A or drill cuttings 116), would be expected to render a value of GASAT as 16.1% or a PORESAT of 16.1%/0.23=70%.

If, upon analysis of the gas present in the return fluid at the surface a GASAT of only 7% is indicated, this suggests the aforementioned flushing phenomenon by the drilling fluid. Thus an actual fmeasured GASAT of 7% would yield an actual PORESAT value=GASAT/$\phi$=7%/0.23=30% PORESAT. Accordingly, the volume flushed by drilling fluid would be 70−PORESAT (actually measured) or 70−30=40, i.e., the volume of fluid flushed into the rock formation between bit teeth penetration. It will be recalled that a nominal expected regional value used for pore saturation is 70 as will now be described in greater detail.

In the Gulf Coast area wherein relatively clean sand reservoirs may be commonly found water comprises nominally 30% of the reservoir pore space with reservoir analyses indicating typical water saturation ranges of between 20%–40% This leaves a nominal 70% or 60-80% range for pore saturation to be occupied by hydrocarbons. Thus in the foregoing calculation in which difference is determined between expected pore saturation and that actually measured from gas in the return fluid and the resultant GASAT value (yielding the volume of fluid flushed by the bit), the aforementioned nominal expected pore saturation value of 70% has been used, which is a fair approximation of what the expected value for this parameter would be. However, it should be readily appreciated that this 70% expected pore saturation value is based upon regional experience and the particular drilling situation encountered. Thus another value (most likely within the range of 60-80%) may be substituted as required for the expected pore saturation value as required in accordance with drilling, field, and regional experience well known in the art.

With the flushing volume given by 70−PORESAT (actually measured) or 70−30, the percentage of volume of the drill cuttings or sample flushed by the drilling fluid will be given by (70−30)/70=57.1% of the volume being flushed by drilling fluid. As previously indicated the fluid flow rate of this drilling fluid into the bottom hole materials which are presumed to be a porous sand or the like will be functionally related to the rate of penetration of the drill bit ROP, and will be given by 57.1%×ROP.

However, it will be recalled that the permeability determination relates a fluid volume flowing through a sample at a rate determined by the pressure differential across the sample. Accordingly, multiplying this linear fluid flow rate of 57.1%×ROP times the porosity $\phi$ will yield the fluid volume Q of drilling fluid flowing through a unit volume of sand, and thus Q=FFR×$\phi$×C. With the fluid volume Q, the viscosity $\mu$ of the drilling fluid, and the pressure differential $\Delta P$ between the mud weight and the pore pressure known, these values may thence be employed in the conventional permeability formula for k used for core sample analysis and previously given to arrive at a permeability value based upon parameters measured during the ongoing drilling operation.

A representative sample of the foregoing technique will hereinafter follow to determine an actual permeability value, employing numbers such as those previously given which might be encountered in typical drilling operation.

---

EXAMPLE $\phi$ = 24%
GASAT = 12%
ROP = 48 ft./hour
$\mu$ = 25 centipoise
MW = 15.7 lbs./gal.
PP = 15.6 lbs./gal.
$\Delta P$ = (MW − PP) × D × .052 = p.s.i.
D = 14,750 ft.
Expected pore saturation = 70%
A = 1cm.$^2$
L = 1cm.

$$Q = \frac{ROP(30.5 \text{ cm/ft.})(1 \text{ cm}^2)(70 - GASAT/\phi)(\phi)}{3600 \text{ sec./hr.} \quad 70}$$

= .0278 cc/sec.

Substituting in:
$$k = \frac{Q \times \mu \times L \times 1000}{\Delta P \times A}$$

we have:
$$k = \frac{.0278 \text{ cc/sec.} \times 25 \text{ centipoise} \times 1 \text{ cm.} \times 1000}{77/14.6969 \text{ atm} \times 1 \text{ sq. cm.}}$$

= 133 md

---

Figure 6:
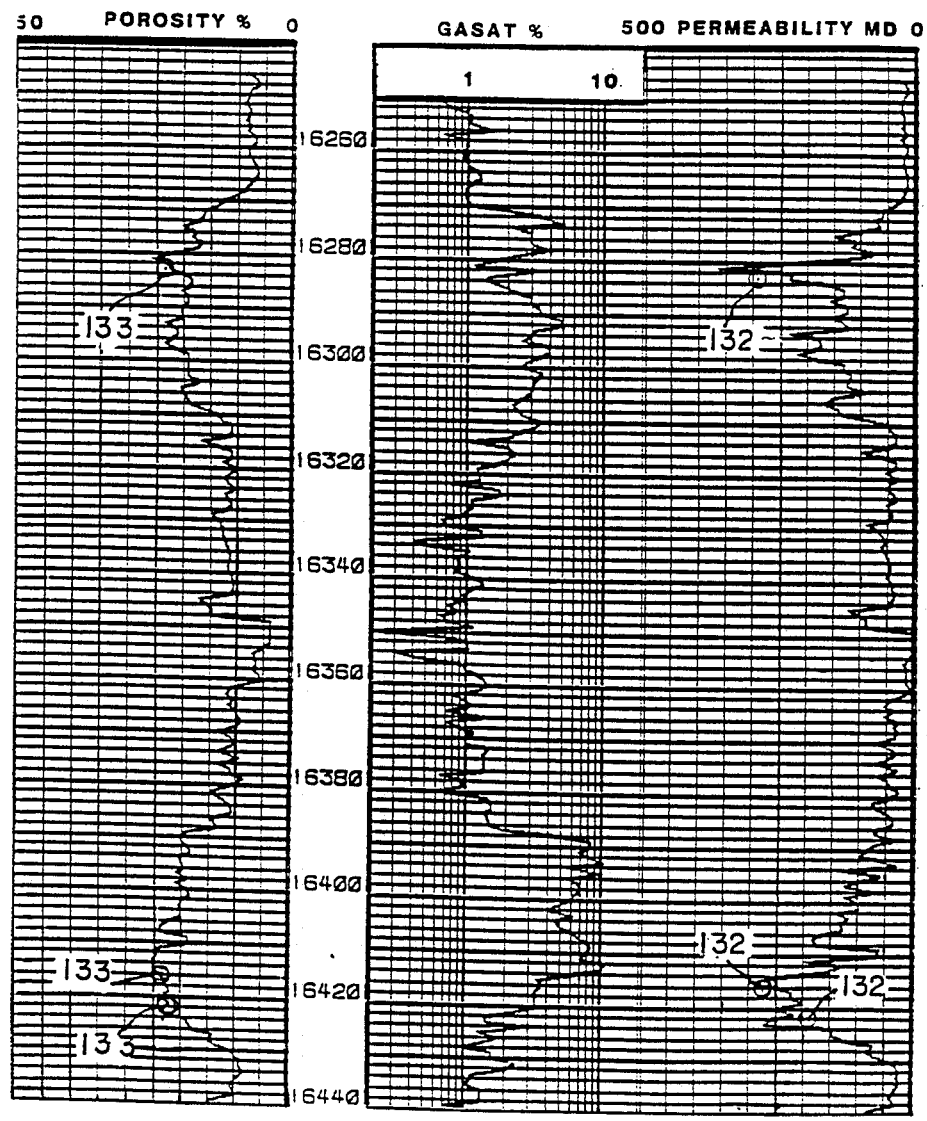
FIG. 6 is a representative well log obtained in accordance with the practice of the present invention, showing correspondence between permeability values determined by the invention and those determined by core sample analysis.

With reference to FIG. 6 there will be seen an actual real time log of a drilling operation over approximately a two hundred foot increment of borehole conducted at a well-site in southern Louisiana. The values shown therein for GASAT were determined in accordance with the techniques of the invention previously described wherein gas content of the drilling fluid was monitored at the surface during the ongoing drilling operation.

Similarly, a portion of FIG. 6 depicts values determined in real time for permeability k also in accordance with the teachings of the present invention wherein the aforementioned GASAT parameters were employed as well as the other parameters just described such as mud viscosity, rate of penetration, and the like.

It is significant to note that after the drilling operation was completed core samples of the well were taken and analyzed in a conventional fashion. Superimposed on the permeability log of FIG. 6 are circles 132 which indicate data points showing permeability values determined by conventional methods of core sample analysis. From a comparison of the log of permeability values determined by the methods of the present invention with these data points 132 derived from core sample analysis, it is striking to note that the results of both techniques are in quite close agreement, thus indicating the validity of the real time permeability determination techniques disclosed herein during the drilling operation.

In like manner, porosity of these cores was determined by conventional core sampling. The porosity values are indicated in the porosity graph of FIG. 6 as circles 133, where the graph is porosity data determined from the actual drilling time in seconds as the time to drill each foot of penetration, functionally related to ROP data in accordance with the technique of the present invention. The close agreement of porosity values determined from such core analysis and drilling time data fuctionally related to ROP data indicates validity of the porosity determination from drilling time data functionally related to ROP.

From the foregoing, it may be understood that the flow of drilling fluid into sand or like permeable formations when drilling is analogous to fluid flow of a test fluid through core samples in conventional laboratory analysis which forms the basis for permeability determined by the herein described methods.

It is therefore apparent that the present invention is one well adapted to obtain all of the advantages and features hereinabove set forth, together with other advantages which will become obvious and apparent from a description of the apparatus itself. It will be understood that certain combinations and subcombinations are of utility and may be employed without reference to other features and subcombinations. Moreover, the foregoing disclosure and description of the invention is only illustrated and explanatory thereof, and the invention admits of various changes in the size, shape and material composition of its components, as well as in the details of the illustrated construction, without departing from the scope and spirit thereof.

What is claimed is:

1. A method of determining at the earth's surface the permeability of a subsurface earth formation having a known nominal hydrocarbon pore saturation value, the formation being tranversed by a borehole resulting from drilling with a drill bit, comprising the steps of:

measuring the rate of penetration of the drill bit through the subsurface earth formation, determining the percentage of hydrocarbon gas saturation for a preselected volume of subsurface fomation displaced by the borehole corrected to the formation pressure and temperature at a predetermined borehole depth functionally related to the measured volume of hydrocarbon gases present in the volume of drilling fluid circulated in the borehole during drilling and displacement of said preselected volume of displaced formation and expressed as a percentage of said preselected volume of displaced formation, determining the drilling time for the drill bit to drill a preselected increment of depth functionally related to the rate of penetration, measuring the viscosity of the circulated drilling fluid, determining the differential pressure between the hydrostatic pressure of the drilling fluid exerted on the bottom of the borehole and the pore pressure of the subsurface formation at the bottom of the borehole, determining an actual formation porosity value functionally related to said drilling time, determining an actual formation pore saturation value for said preselected volume of displaced formation at a predetermined borehole depth functionally related to the measured values of hydrocarbon gas saturation and actual formation porosity, determining the percentage of said preselected volume of displaced formation at said predetermined depth flushed by said ciculating drilling fluid functionally related to the known nominal value of the formation pore saturation and said measured actual value of the formation pore saturation, determining the linear fluid flow rate of said circulated drilling fluid through a preselected volume of the subsurface formation displaced by the borehole at a predetermined depth and functionally related to said determined drilling fluid flush volume percentage, the rate of penetration of the drill bit and said actual measured value of formation porosity, determining the volume of drilling fluid flowing through said preselected volume of displaced formation at said linear fluid flow rate, and determining the permeability of the subsurface earth formation for said preselected volume of displaced formation at said predetermined depth and functionally related to the determined volume of drilling fluid flowing through said preselected volume of displaced formation, said viscosity of the drilling fluid and said differential pressure.

2. The method as described in claim 1, wherein said step of determining the percentage of hydrocarbon gas saturation is determined in accordance with the following equation:

$$\%GASAT = \frac{(\%GAS)(Bbl\ Mud)(5.6146)(14.65)(460 + BHT)}{(14.65 + BHP)(460 + 100)} \times \frac{1}{(0.00545\ D)}$$

where:

% GASAT = volume of hydrocarbons present in a cylindrical subsurface formation volume having an increment depth of one foot, expressed in percent;

% GAS = volume of hydrocarbon gases per barrel of circulated drilling fluid at earth surface conditions, expressed in percent;

Bbl Mud = volume of drilling fluid circulated in the borehole per vertical foot of borehole drilled;

BHT = bottomhole temperature in ° F. at a selected borehole depth; and

BHP = bottomhole pressure in psi at a selected borehole depth; and

D = drill bit diameter in inches.

3. The method as described in claim 1, wherein said step of determining an actual formation porosity value is determined in accordance with the following equation:

$$\phi = 100 - (\log_{10} T \times C_1)$$

where:

$\phi$ = formation porosity expressed in percent;

T = drilling time in seconds and functionally related to ROP as the time to drill each foot of penetration of the drill bit; and $C_1$ = a dimensional constant equal to 28.12.

4. The method as described in claim 1, wherein said step of determining an actual formation pore saturated value is determined in accordance with the following equation:

$$\%PORESAT(actual) = \%GASAT/\phi(f)$$

where:
- % PORESAT(actual) = actual formation pore saturation expressed in percent;
- % GASAT = volume of hydrocarbon present in a cylindrical subsurface formation of predetermined volume, expressed in percent; and
- $\phi(f)$ = formation porosity expressed in fractional units.

5. The method as described in claim 1, wherein said step of determining the drilling fluid flush volume percentage is determined in accordance with the following equation:

$$\%FLSHVOL = \frac{\%PORESAT(known) - \%PORESAT(actual)}{\%PORESAT(known)}$$

where:
- % FLSHVOL = the volume of the subsurface formation from which hydrocarbons have been flushed by the drilling fluid, expressed in percent;
- % PORESAT(known) = the nominal value of hydrocarbon pore saturation known for the reservoir and based on reservoir engineering concepts, expressed in percent; and
- % PORESAT(actual) = the actual measured value of hydrocarbon pore saturation for the formation functionally related to the drilling time.

6. The method as described in claim 1, wherein said step of determining the linear fluid flow rate of the drilling fluid through the formation is determined in accordance with the following equation:

$$FFR = \%FLSHVOL \times ROP$$

where:
- FFR = linear fluid flow rate of the circulated drilling fluid through a preselected volume of the subsurface formation displaced by the borehole at a predetermined borehole depth;
- % FLSHVOL = the volume of the subsurface formation from which hydrocarbons have been flushed by the drilling fluid, expressed in percent; and
- ROP = rate of penetration of the drill bit in feet per hour.

7. The method as described in claim 1, wherein said step of determining the volume of drilling fluid flowing through said preselected volume of displaced formation at said linear fluid flow rate is determined in accordance with the following equation:

$$Q = FFR \times \phi(f) \times C$$

where:
- Q = the volume of drilling fluid flowing through a preselected volume of displaced formation at a predetermined linear fluid flow rate expressed in cubic centimeters per second;
- FFR = linear fluid flow rate of the circulated drilling fluid through a preselected volume of the subsurface formation displaced by the borehole at a predetermined borehole depth;
- $\phi(f)$ = formation porosity expressed in fractional units; and
- C = a dimensional constant for converting to metric units.

8. The method as described in claim 1, wherein said step of determining the permeability of the subsurface formation is determined in accordance with the following equation:

$$k = \frac{Q \times \mu \times L \times 1000}{\Delta P \times A}$$

where:
- k = formation permeability measured in millidarcies;
- Q = volume of fluid flowing through a preselected volume of displaced formation at a predetermined linear fluid flow rate:
- $\mu$ = the viscosity of the drilling fluid measured in centerpoise units;
- L = length of the unit volume of the isplaced formation;
- $\Delta P$ = the differential pressure determined as the difference between the hydrostatic pressure of the drilling fluid and the pore pressure of the formation at the bottom of the borehole converted to atmosphere units; and
- A = the cross-sectional area of flow through the unit volume of the displaced formation.

* * * * *